United States Patent [19]

Stewart et al.

[11] Patent Number: 4,687,337
[45] Date of Patent: Aug. 18, 1987

[54] ATMOSPHERIC AEROSOL EXTINCTIOMETER

[75] Inventors: Harold S. Stewart, No. Andover; Donald F. Hansen, Needham; Vernon D. Turner, Lincoln, all of Mass.

[73] Assignee: The United States of America as represented by the Secretary of the Air Force, Washington, D.C.

[21] Appl. No.: 298,687

[22] Filed: Sep. 2, 1981

[51] Int. Cl.⁴ .............................................. G01N 21/61
[52] U.S. Cl. .................................... 356/437; 250/345; 250/575
[58] Field of Search ............... 356/434, 437, 438, 439, 356/440, 435; 250/343, 345, 565, 575

[56] References Cited

U.S. PATENT DOCUMENTS

| | | | |
|---|---|---|---|
| 2,803,752 | 8/1957 | Warren | 250/209 |
| 3,091,690 | 5/1963 | McHenry | 250/575 |
| 3,725,204 | 4/1973 | Marshall, Jr. et al. | 195/127 |
| 3,746,452 | 7/1973 | Teboul et al. | 356/201 |
| 3,761,724 | 9/1973 | Dennis | 356/434 |
| 3,937,962 | 2/1976 | Faulhaber et al. | 250/346 |
| 4,008,394 | 2/1977 | Risgin et al. | 250/345 |
| 4,014,612 | 3/1977 | Atwood et al. | 356/435 |
| 4,023,909 | 5/1977 | Ross | 356/205 |
| 4,111,560 | 9/1978 | Jolanki et al. | 356/243 |
| 4,176,963 | 12/1979 | Fabinski et al. | 356/435 |
| 4,180,733 | 12/1979 | Veda | 250/345 |
| 4,256,964 | 3/1981 | Ishida et al. | 250/345 |
| 4,264,209 | 4/1981 | Brewster | 356/416 |
| 4,283,142 | 8/1981 | De Steur et al. | 356/434 |
| 4,329,048 | 5/1982 | Capitini et al. | 356/73 |
| 4,371,785 | 2/1983 | Pedersen | 250/343 |

FOREIGN PATENT DOCUMENTS

1038,376  8/1966  United Kingdom ............... 250/575

Primary Examiner—R. A. Rosenberger
Attorney, Agent, or Firm—Willard R. Matthews; Donald J. Singer

[57] ABSTRACT

The extinction coefficient of atmospheric aerosol is measured by an instrument in which a single light beam from a graybody source is alternately directed through two similar optical paths to a detector. Each optical path traverses an equal length region of ambient air. Aerosols are filtered from the ambient air region of one optical path. The detector measures the modulation of the incident radiation and its output is a function of the extinction coefficient of the ambient air under test. A second detector is used to monitor the beam power. Processing electronics compute the extinction coefficient of the ambient air under test from the detector outputs. The ambient air regions of the two beam paths are alternately filtered for improved performance.

1 Claim, 4 Drawing Figures

ATMOSPHERIC AEROSOL EXTINCTIOMETER

STATEMENT OF GOVERNMENT INTEREST

The invention described herein may be manufactured and used by or for the Government for governmental purposes without the payment of any royalty thereon.

BACKGROUND OF THE INVENTION

This invention relates to atmospheric transmission measurements and to means for determining the component of infrared atmospheric attenuation arising from aerosol extinction. Specifically, the invention comprehends an extinctiometer for measuring the infrared extinction coefficient of atmospheric aerosols.

The greatest uncertainty in the application of computer models to the on-site calculation of the transmission of infrared radiation over optical paths of military significance in tropospheric situations is in the wavelength dependent attenuation of optical radiation by atmospheric aerosol particles. The attenuations due to the molecular constitutents of the atmosphere are known in the case of the uniformly mixed gases ($N_2$, $C_2$, $CO_2$, $N_2O$, $CO$, $CH_4$) or are readily calculable from standard meteorological measurements in the cases of the non-uniformaly mixed molecules ($H_2O$, $O_3$). No suitable instrument appears to be available which will measure atmospheric aerosol extinction coefficients over the environmental range required for military requirements. Measurements from such an instrument, if one existed, would provide invaluable inputs for on-site model predictions of infrared atmospheric transmissions.

There currently exists the need for a method and means for determining the component of infrared atmospheric attenuation arising from aerosol extinction using measurements made with equipment located at a single point on or near a transmission path of interest. The single-point constraint rules out conventional transmissometers as well as bi-static or multi-static laser or searchlight measurements.

For military applications such an instrument is required to be a compact device, operable in outdoor environments from surface levels to 5 km altitude and is to have sufficient dynamic range of sensitivity to cover conditions ranging from fog to 50 km visibility. The preferred technique is a direct measurement of aerosol extinction coefficients although the possibility of separate determinations of aerosol scattering and absorption coefficients is not ruled out. The wavelength region of interest is typically 1-12 micrometers with emphasis on the 1, 1 the 3-5 and the 8-12 micrometer regions. The instrument must sample ambient air which, in the process of sampling, is unperturbed in terms of temperature, relative humidity, number density of aerosol particles and their size distribution. It must be operable unattended for long periods, without frequent operator intervention for calibration or repair.

It is required that equipment located at one point make measurements from which the component of atmospheric attenuation due to aerosol extinction along a path can be deduced. Solutions to this problem fall into several classes. One class of solutions involves measuring atmospheric transmission. A measurement of atmospheric transmission convolves both the aerosol and molecular components of atmospheric attenuation. The attenuation due only to aerosol extinction is then derivable if the attenuation due to molecular constituents can be estimated or calculated.

Two other classes of solutions are (1) a direct measurement of the optical attenuation parameters of aerosols; i.e. the aerosol extinction coefficient, or separate measurements of the scattering and absorption coefficients, and (2) measurement of the physical parameters of the aerosols with a derivation of the optical extinction.

The simplest method for measurement of atmospheric transmission involves targets of opportunity such as hills, barns, skyscrapers, lighthouses, cathedrals, ships, islands, and the sea horizon. These are the natural visibility targets which have been used for the rather subjective visibility estimates made at airports, and at sea. Instruments exist with which transmission along the path to such a target can be determined by measuring the contrast of the target against the horizon sky background. In general this is a daytime technique and in practice its use has been limited to the visible portion of the spectrum. Such observations are passive in that no optical radiations are projected from the measuring point. Passive observations are sometimes desirable because of the security; i.e., they do not expose the location of the measuring equipments.

A second method for determining the transmission of an atmospheric path involves use of single-ended active equipment. The equipment involves both a projector of radiation along the path and a detector of radiation backscattered by the atmosphere. Usually short laser pulses are used and the time history of backscattered radiation is analyzed to deduce the transmission of the path. Such lidar systems can provide values of path transmission which are based on physical measurements and are calculated using some approximations and assumptions. Paths so investigated can be horizontal, vertical, or slant and the results obtained do not depend on a model of the atmosphere. Lidar systems, which might meet some of the requirements stated above are massive and require frequent, if not constant, attention from an operator. Furthermore they are active systems and not secure.

Measurements of atmospheric aerosol extinction can take two different approaches. In a first approach separate local values of the scattering coefficient and the absorption coefficient can be measured or the local value of the extinction coefficient (which is the sum of the scattering coefficient and the absorption coefficient) at the wavelength or within the wavelength band of interest can be measured. If measurements are made at only one point on the path of interest than an atmospheric model is required to generate values of the extinction coefficient for the other points along the path. Usually such models are based on changes of aerosol characteristics with changes of atmospheric pressure, temperature and relative humidity as well as changes of the aerosol number density, size distribution and complex refractive index and these, in turn, cause changes in values of the extinction coefficient. A second approach, the measurement of the physical parameters of aerosols is similar to the one just outlined except that physical parameters rather than optical parameters of the atmosphere are measured at one end of the path in question. The physical parameters are aerosol size distribution, number density and composition. Rather than composition of the aerosols their complex refractive index is usually given since this is the critical aspect of composition if the aerosol particles are treated as homogeneous spheres. Knowledge of the physical parameters results in somewhat better correlations of changes in the calculated extinction coefficients to changes in the meteorological conditions. The extinction coefficient at any wavelength can be calculated from the data on aerosol size distribution and concentration if only the real and the imaginary indices of refraction are known at each wavelength and for the various sizes of aerosols. Measuring these indices is difficult and it is usual practice to assign index values appropriate to the weather, the season, the history of volcanic action and the region of the world for which the calculations are being made. The changes in size distribution which occur with changes of meteorological parameters (pressure, temperature, relative humidity) can be predicted if the composition of the aerosols is known. The complex index of refraction is also a function of composition. It may be argued that measurement of the physical parameters of the aerosols is more basic than measurement of optical parameters and this is so. However, the real time measurement of aerosol composition which is required to calculate complex refractive index as a function of wavelength is a difficult task. The complex index is very important throughout most of the infrared where values of the single scattering albedo, which is a function of the imaginary index, are significantly less than one. In view of the stringent device requirements given and the various deficiencies attendant to "measurement of contrast", "Lidar" and "point measurements of physical parameters" techniques "point measurement of optical parameters of the atmospheric aerosols" is seen to be the most suitable approach to realizing the extinction measurement requirements.

An extensive literature survey has revealed that the various possible instruments for fulfilling the extinction measurement requirements can be grouped into five main groups as follows:
 1. Extinctiometer
 2. Transmissometer
 3. Nephelometer
 4. Spectophone
 5. Lidar The first of these is the subject of the present invention and will hereinafter be described in detail. The literature survey has not found any reference to an equivalent device, indicating that operable extinctiometers of the type considered are presently beyond the state of the art. The extinctiometer is thus unique both in its approach to the measurements problem and in the fact that no known effort has been made to construct a workable instrument based on this concept. Transmissometers exist in a variety of configurations, commonly employing a light source separated from a receiver by the scattering/absorbing medium being measured. The spectral region covered is determined by the light source/filter combination. Long-path transmissometers violate the requirements for compactness, leaving for consideration only the so-called White cell instruments. These employ multiple reflections to achieve a folded path, which approaches the conditions of the long path devices within the confines of a small instrument. The combination of both scattering and absorption, i.e., extinction, is measured. In contrast to this, nephelometers measure only the scattering component of extinction. A number of highly sensitive varieties of this instrument have been developed, including the integrating, polar, and fixed angle nephelometers. Some of these enable separation of the aerosol scattering component by reference to filtered ambient air. Most operate in the visible or near IR spectral regions and make use of incoherent light sources. Spectophones, which measure only the absorption component of extinction, make use of the pressure rise in the absorbing gas due to its being heated by the absorption process. Pressure rise is sensed either with a manometer or microphone, yielding a highly sensitive means of measuring the absorption coefficient. A great variety of spectrophone devices exist, including pulsed and CW types, and these instruments have been operated over a wide spectral region from the visible to the mid IR at 10 $\mu$m. Although most spectrophones employ lasers, this is not essential to their operation.

The final instrument type here considered is the lidar, of which there are many varieties. These narrow-beam laser devices measure the backscattered signal from atmospheric scattering and, under proper circumstances, serve to derive the atmospheric transmission for a portion of the laser beam path. In effect, these devices can become single ended transmissometers. Most lidars are short-pulse devices, although one variant is used in CW mode. Some employ Doppler techniques, and some make use of a Raman scatter from specific molecules. Lidars have undergone extensive and highly sophisticated development in the course of the past decade, and show promise for a potentially unique capability for application to the aerosol extinction problem. However, their development at the present time does not satisfy some of the operational requirements, i.e. those related to compactness, field worthiness, and maintainability.

To summarize the above instrument groupings: The extinctiometer and the various transmissometer instruments, including lidars, provide a direct measurement of atmospheric extinction of transmission. The extinctiometer and some transmissometers provide for separating the aerosol extinction from that of the ambient air, whereas in general, lidars do not provide such a separation. Both nephelometers and spectrophones are highly developed, ultra-sensitive, devices for measuring atmospheric scattering (nephelometers) and absorption (spectrophones). For an extinction determination it would be necessary to employ a combination of these two instrument types. Each individually has the advantage of a high state of development and well-demonstrated sensitivity at the levels required for the present application. Neither instrument type requires the use of a laser, although most spectrophone applications have to date employed laser sources. Both nephelometers and spectrophones have been used in a differential mode which separate the effects of aerosols from those of ambient air. Whereas spectrophones have been extensively exploited over the full spectral range required (1-12 microns), most nephelometer applications have been in the visible and near IR regions.

It is seen therefore that the current state-of-the-art does not provide suitable means for obtaining effective accurate atmospheric transmission measurements for the requirements and conditions stated above. Accordingly, there presently exists the need for an extinctiometer that satisfies these requirements. The present invention is directed toward satisfying that need.

SUMMARY OF THE INVENTION

The invention is an extinctiometer having: a light source for providing a beam of radiant energy in a closed transmitter housing; a monitor detector and signal detector in a closed receiver housing; an optical system establishing two similar parallel paths (A) and (B) for the beam between the light source and the detectors; and a rotatable sector mirror that alternatively switches the beam through paths A and B. The receiver housing is spaced a distance L from the transmitter housing establishing a region of ambient air that both light paths traverse. Windows are provided in the transmitter and receiver housings to accommodate passage of the beam. An open ended filtered air container is positioned to filter the ambient air in the vicinity of paths A and B alternately.

The general equation for the extinction coefficient generated by the extinctiometer of the invention is developed as follows:

If $P_o$ is the power projected by the light source then, in the absence of aerosol extinction some fraction $\alpha$ would arrive at the detector via path A and some fraction $\beta$ would arrive via B. If L is the length of the open ended container and $\gamma$ is the aerosol extinction coefficient then the peak to peak modulation $S_1$ is given by $$S_1 = \alpha P_o - \beta P_o e^{-\gamma L} \quad (1)$$

When the filter air container is moved from beam path A to beam path B the peak to peak modulation $S_2$ is given by $$S_2 = \alpha P_o e^{-\gamma L} - \beta P_o \quad (2)$$

by using synchronous rectification in the modulation detector the signs (+ or −) or $S_1$ and $S_2$ are preserved. Then $$S_2 - S_1 = (\alpha + \beta) P_o e^{-\gamma L} - P_o(\alpha + \beta) \quad (3)$$

assuming a beam splitter in which reflection equals transmission at 45° incidence then the monitor signal M is $$M = P_o (\alpha + \beta)/2 \quad (4)$$

except for a correction of $e^{-\gamma L}$ in one or the other beam. Since $1 - e^{-\gamma L} < 10^{-4}$ for all cases of interest this correction may be neglected and $$\gamma L \approx 1 - e^{-\gamma L} = S_1 - S_2/2M$$

or $$\gamma = S_1 - S_2/2LM \quad (5)$$

It is a principal object of the invention to provide a new and improved atmospheric aerosol extinctiometer.

It is another object of the invention to provide an extinctiometer that will measure atmospheric aerosol extinction over an environmental range that meets military requirements.

It is another object of the invention to provide an extinctiometer that is compact, is operable in outdoor environments from surface levels to 5 km altitude and has sufficient dynamic range of sensitivity to cover conditions ranging from fog to 50 km visibility.

It is another object of the invention to provide an extinctiometer of the type described that provides direct measurement of aerosol extinction coefficients in the wavelength region of 1-12 micrometers.

It is another object of the invention to provide an extinctiometer of the type described capable of sampling ambient air which, in the process of sampling is unperturbed in terms of temperature, relative humidity, number density of aerosol particles and their size distribution.

It is another object of the invention to provide an extinctiometer of the type described that will be operable unattended for long periods without frequent operator intervention for calibration or repair.

These together with other objects, features and advantages of the invention will become more readily apparent from the following detailed description taken in conjunction with the illustrative embodiments in the accompanying drawings.

DETAILED DESCRIPTION OF THE PREFERRED EMBODIMENTS

The purpose of the invention is to provide an instrument that measures the extinction coefficient of atmospheric aerosols. The extinction coefficient of aerosols is composed of both the scattering and absorption coefficients. An extinctiometer measures the combined attenuation in a beam of optical radiation due to the absorption and scattering properties of the aerosols present in the beam. The instrument comprehended by the invention is so designed and operated that the scattering and absorption effect due to molecular constituents normally present in the atmosphere ($O_2$, $N_2$, $CO_2$, $O_3$, $N_2O$, $CO$, $CH_4$, and $H_2O$) are cancelled out of the measurement by the use of a dual beam arrangement. The extinctiometer differs from a transmissometer in that an extinctiometer measures the amount of radiation removed from an optical beam, a transmissometer measures the amount of radiation remaining in the beam.

Figure 1:
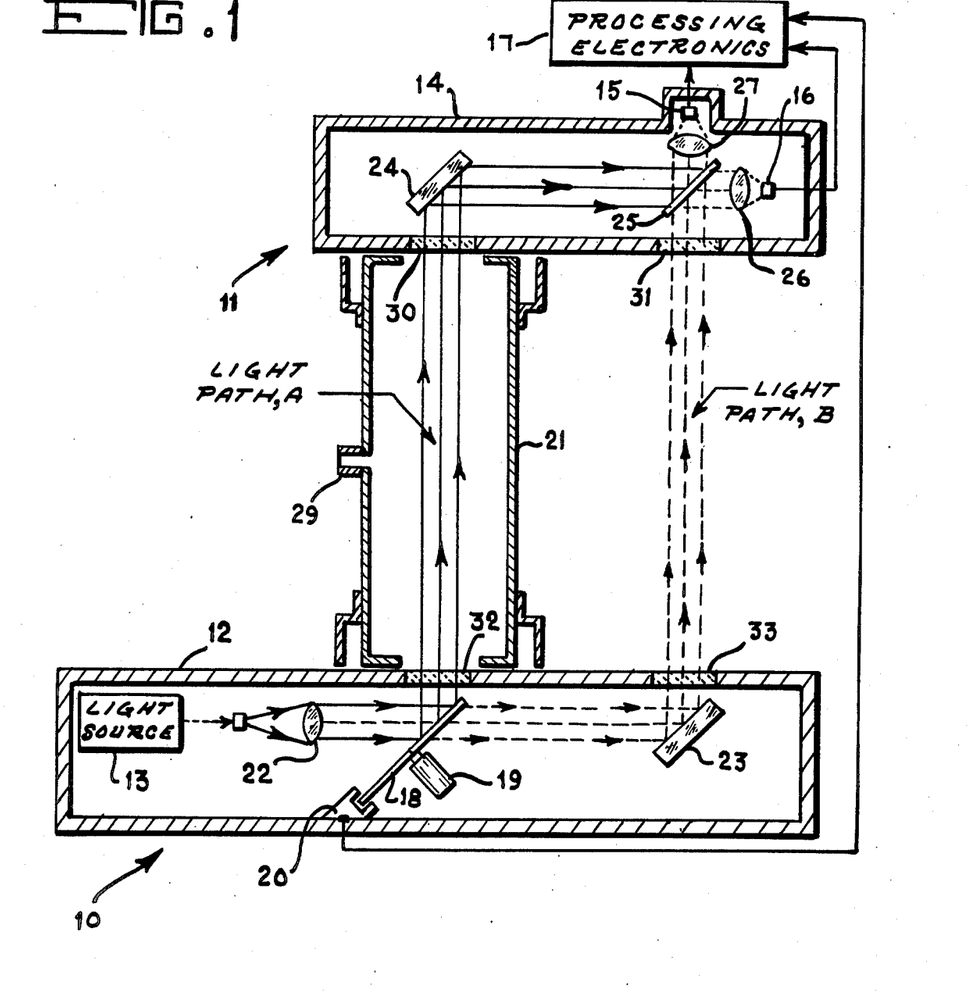
FIG. 1 is a sectional view of one embodiment of the extinctiometer of the invention.
Figure 2:
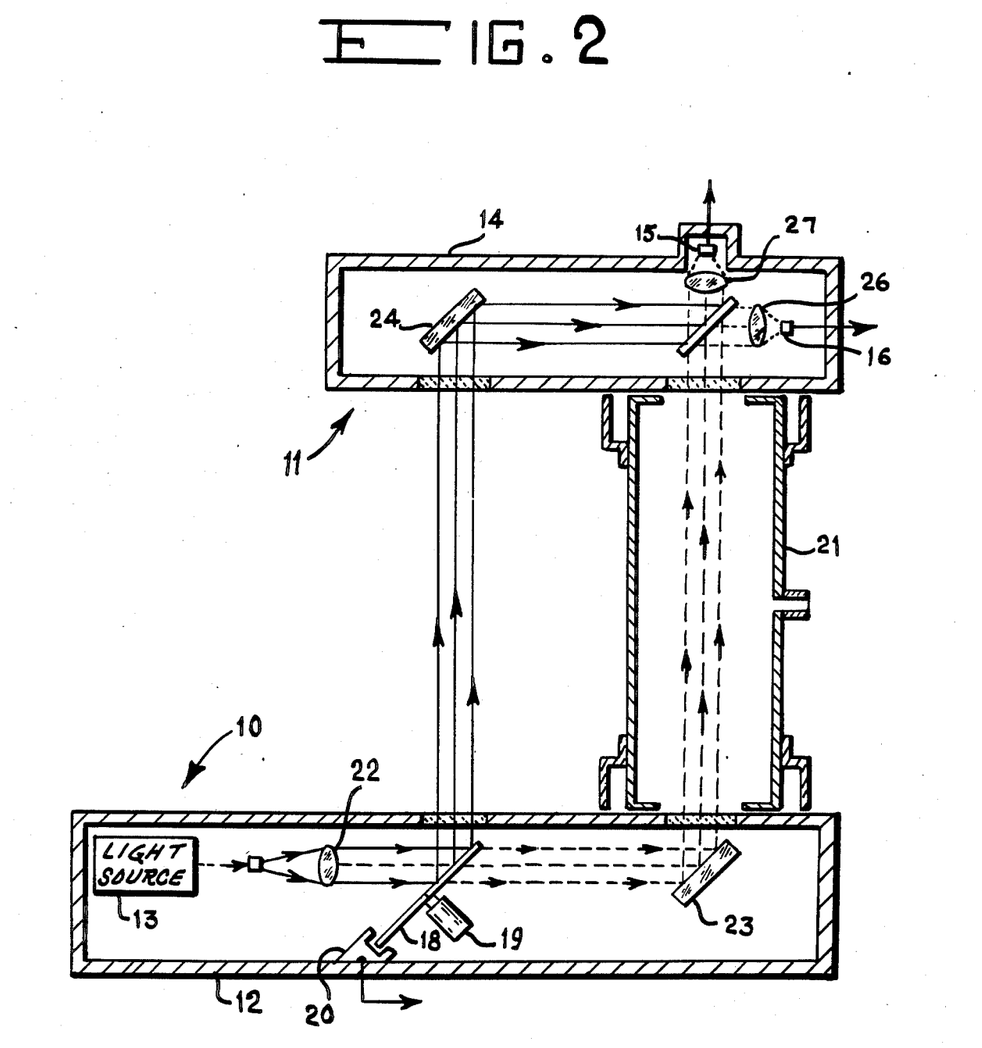
FIG. 2 is the sectional view of the embodiment of FIG. 1 with the air filter in an alternate position.
Figure 3:
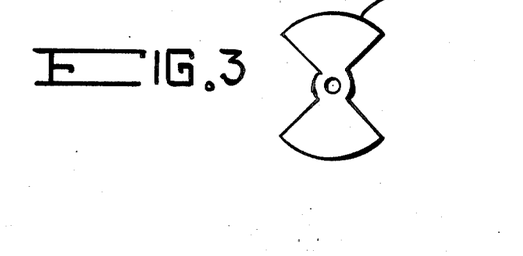
FIG. 3 is a detail of the rotatable sector mirror of the extinctiometer of FIG. 1.

The essential elements of the extinctiometer of the invention are shown in the sectional view of the embodiment of FIG. 1. These comprise transmitter 12, receiver 11, open ended container 21, and an optical system. Transmitter 12 consists of a sealed housing 12 having windows 32, 33, light source 13, rotatable sector mirror 18 driven by motor 19, synchronous pick up 20, and a portion of the optical system including lens 22 and mirror 23. Open ended container 21 has a fixture 29 through which filtering of the ambient air in the region of light path A is accomplished. Open ended container 21 can be moved to enclose the region of light path B as shown in FIG. 2. Receiver 11 consists of sealed housing 11 having windows 30, 31, light detectors 15, 16, a portion of the optical system including mirror 24, beam splitter 25 and lenses 26, 27, and processing electronics 17. Processing electronics 17 can be any suitable electronic or computer means for resolving the equations hereinafter developed from signal values received from detectors 15, 16 and synchronous pick up 20. Transmitter 10 and receiver 11 are maintained in position by appropriate structure or brackets (not shown).

The extinctiometer described above has been designed to measure the extinction coefficient of the aerosols in the free atmosphere. By way of example a specific embodiment of the invention hereinafter described is designed for measurements to be made in three wavelength bands centering on 1μ, 3μ and 10μ. The design principles discussed in this section involve a single black-body (or gray body) used as source for the three wavelength bands, a single optical system, except for the filters used to isolate the wavelength bands, and a single pair of radiation detectors. The extinction measurement does not include molecular scattering or absorption.

The minimum values of extinction coefficient, $\gamma$, which are of interest at the three wavelengths are:

$$\gamma_{10} = 1.5 \times 10^{-8} \text{ cm}^{-1} \text{ at } \lambda = 10\mu \quad (6)$$

$$\gamma_3 = 3 \times 10^{-8} \text{ cm}^{-1} \text{ at } \lambda = 3\mu$$

$$\gamma_1 = 3 \times 10^{-7} \text{ cm}^{-1} \text{ at } \lambda = 1\mu$$

The error in $\gamma/\Delta\gamma$ is to be less than 20 percent of $\gamma$. That is:

$$|\Delta\gamma/\gamma| < 0.2 \quad (7)$$

The design principles of the instrument are illustrated in FIG. 1. In the instrument disclosed thereby light travels alternately along two similar paths A and B as shown. Choice of path is determined by the angular position of rotating sectored-mirror 18. The two paths are recombined by beam splitting mirror 25 so that each detector 15, 16 behind the beam splitter receives light alternately from the two paths. Any difference in the power transmitted by the two paths will result in an AC component in the detector 16 output with frequency equal to that of the chopper and amplitude equal to the power difference. With such a set-up the transmission of a sample can be measured by introducing it into one beam and measuring the change in the AC current and the value of the DC current. A more accurate measurement results if the measurement is made with the sample in one beam and again with the sample in the other beam. This is accomplished by translating open ended container 21 to the position shown in FIG. 2 as described below. The ambient air sample is assumed to contain both aerosol and molecular attenuators. In FIG. 1 the sample is in path B. Path A, which passes through the open ended container 21 is free of aerosols because the container is fed filtered air through fixture 29 by conventional air filtering equipment (not shown). The molecular composition of the two paths is assumed to be the same. As a second step in the measurement, the open-ended container 21 is moved from path A to path B (FIG. 2). A sample path length of 50 cm is assumed.

If $P_o$ is the radiant power projected by a perfect source system, then, when the sector mirror 18 is completely in the projected beam, some fraction of $P_o$ reaches the detector by path A. Let that fraction be $AP_o$. When the sectored mirror is completely out of the beam then some fraction of $P_o$, $BP_o$, reaches the detector. If the mirror sectors and the open sectors are equal in angular extent, then the average power incident on the detector, $\bar{p}$, is $$\bar{P} = P_o(A+B)/2 \quad (8)$$

Then the power p(t) incident on the detector may be written $$p(t) = \bar{p} \pm |A - B| P_o/\pi \cos(2\pi ft) \quad (9)$$

where f is the frequency of chopping. The term $|A-B|P_o/\pi \cos(2\pi ft)$ is the fundamental component which has an rms value of $$p_{rms} = \sqrt{2}/2\pi (A - B) P_o \quad (10)$$

When a sample of length L and extinction coefficient $\gamma$ is introduced in path A, the lower incident of the detector becomes $$p(t)_A = P_o\left(\frac{Ae^{-\gamma L} + B}{2}\right) + \frac{(Ae^{-\gamma L} - B)P_o}{\pi} \cos(2\pi ft) \quad (11)$$

and $$P_{rms\,A} = \frac{\sqrt{2}}{2\pi} (A e^{-\gamma L} - B) P_o \quad (12)$$

With the sample in path B $$P_{rms\,B} = \frac{\sqrt{2}}{2\pi} (A - B e^{-\gamma L}) P_o \quad (13)$$

If the rms detector output signal at frequency f is Vrms, then in general $$V_{rms} = R_f P_{rms} \quad (14)$$

where $R_f$ is the detector responsivity at frequency f (and at the wavelength of the incident power). The two signals $V_{rms\,A}$ and $V_{rms\,B}$ corresponding to the sample being in path A and again in path B are $$V_{rms\,A} = R_f\left\{\frac{\sqrt{2}}{2\pi}(A e^{-\gamma L} - B) P_o\right\} \quad (15)$$

and $$V_{rms\,B} = R_f\left\{\frac{\sqrt{2}}{2\pi}(A - B e^{-\gamma L}) P_o\right\} \quad (16)$$

The quantity $V_{rms\,B} - B_{rms\,A}$ is just $$V_{rms\,B} - V_{rms\,A} = \frac{\sqrt{2}}{2\pi} P_o R_f(A + B)(1 - e^{-\gamma L}) \quad (17)$$

In the cases of interest here $\gamma L << 1$ so $$\frac{\sqrt{2\pi}(V_{rms\,B} - V_{rms\,A})}{P_o R_f(A + B)} = \gamma L \quad (18)$$

The incident of DC power is $$P_o \frac{A e^{-\gamma L} + B}{2} \text{ or } P_o \frac{A + B e^{-\gamma L}}{2}$$

and since $\gamma L << 1$ we take the DC signal, $V_{DC}$, in either case to be $$V_{DC} = R_o P_o \left( \frac{A + B}{2} \right) \qquad (19)$$

where $R_o$ is the DC responsivity of the detector used to measure the DC component of the incident power. Finally:

$$\gamma = \frac{\sqrt{2} \, \pi R_o}{2 R_f} \frac{V_{rms\,B} - V_{rms\,A}}{L \, V_{DC}} \qquad (20)$$

There are two signals given by Equations (15) and (16) above. In each case the noise is determined by the NEP of the detector added statistically to the statistical variations in photon arrival rate. The noise equivalent power (NEP) of the detector includes 300° K. radiation exchange noise between detector and background so at $10\mu$ only the statistics of the signal photons need attention.

Figure 4:
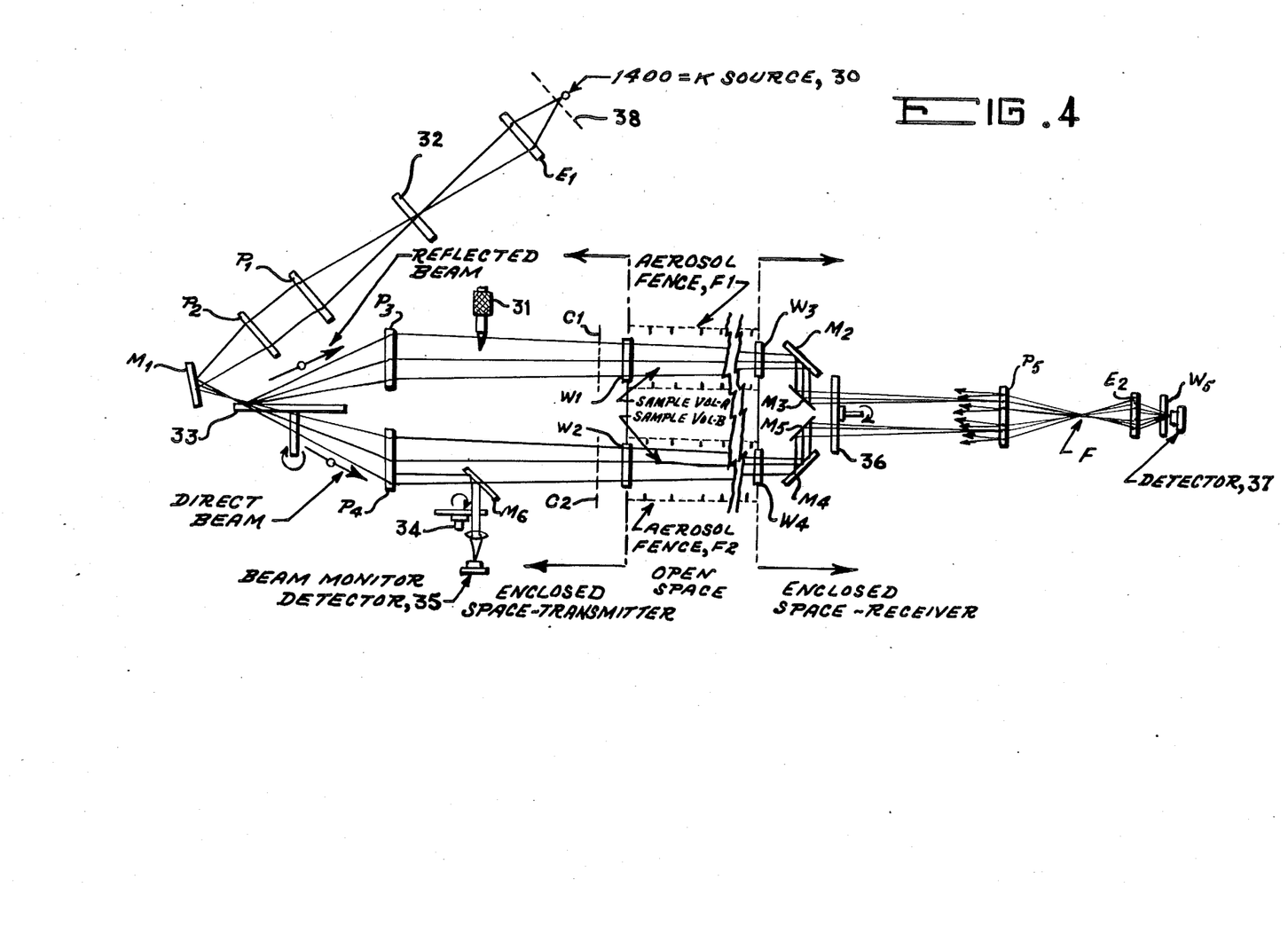
FIG. 4 is a schematic diagram of another embodiment of the invention.

A specific embodiment of the invention is illustrated schematically in FIG. 4. Shown therein is a balanced two beam extinctiometer consisting of a light source 30, two blade reflecting chopper 33, beam monitor detector 35, beam micro balance 31,, signal detector 37, an optical system for establishing two light paths between light source 30 and signal detector 37, and air filter means comprised of aerosol fences F1 and F2. The optical system comprises source window 38, 4 mm diameter aperture 32, off axis parabolic mirrors P1, P2, plane tuning mirror M-1, off axis parabolic mirrors P3, P4, plane mirror M6, windows W1, W2, W3, W4, plane tuning mirrors M2, M3, M4, M5, off axis parabolic mirror P5, elliptical mirror E2 and detector window W5. Spectral regions of operation are selectable by means of three position filter wheels 34, 36.

In operation, radiation from a high temperature gray body source 30 is imaged by elliptical mirror E1 onto a 4 millimeter diameter field stop aperture 32 at 2:1 conjugates transforming the f/2 collecting aperture into an f/4 bundle. A pair of off-axis parabolic mirrors P1 and P2 re-image the field stop at a point ahead of a rotating reflective chopper wheel 33. Radiation is alternately transmitted and reflected by the chopper wheel 33 to a second pair of off-axis parabolic mirrors P3 and P4 which relay the wheel 33 to a second pair of off-axis parabolic mirrors P3 and P4 which relay the (not two) images of the field stop onto a parabolic field mirror P5. In passing from mirror P3 and P4 to P5 the two beams are required to transit the sample volumes A and B. Turning mirrors M2–M5 lessen the separation between the two beams and by slight tilts direct the beams to P5 such that principal rays from the centers of the two mirrors P3 and P4 become axial rays allowing P5 to form coincident images of the two aperture stops P4 and P5 at image point F. A second elliptical mirror E2 then reimages the image point F onto the pyroelectric detector 37. The relative aperture of each bundle of radiation reaching the detector is f/2 and the geometric image is a circle 2 millimeters in diameter.

Reducing the separation between beams with mirrors M2–M5 permits the use of a single field mirror P5 and permits the use of a single filter wheel for both beams. The filter wheel 36 is located immediately after mirrors M3 and M5 in radiation bundles having minimum amounts of divergence.

Four windows W1–W4 are necessary to provide environmental protection for the optical and electronic components housed in the transmitting and receiving enclosures. The windows must transmit radiation from 1 to 12 microns and be capable of withstanding environmental effects for a reasonably long period of time before resurfacing or replacing. ZnSe has been selected as the material most suitable for fulfilling these two requirements.

By way of example, details and specifications for the principal elements of the system are hereinafter described in some detail. It is noted, however, that other specifications and other suitable components can also be utilized and that the present invention is not limited to the specification and components given.

The primary detector 37 is of the pyroelectric type having a 3 millimeter diameter sensing element. The detector is housed in an enclosure which is sealed with a $B_aF_2$ window to prevent air motion around the detector. The detector also has a $B_aF_2$ window to further reduce air motion from reaching the sensing element. The detector is mounted inside a detector enclosure in a manner which will minimize thermal convection and conduction, secure accoustic and vibration isolation, and provide maximum EMI protection.

The radiation incident on the primary detector is essentially DC (i.e. unmodulated) radiation. The specifications for detector 37 are as follows:

| Type | Pyroelectric |
| --- | --- |
| Wavelength Range | 0.9 to $12\mu$ |
| Element Size | 3 mm diameter |
| Permanent Window | $B_aF_2$ |
| NEP (0.9–$12\mu$, 34 Hz; 1 Hz BW) | $10^{-9}$ W/Hz$^{\frac{1}{2}}$ |
| Voltage Responsivity | 43 V/W |
| Temperature Range | $-20$ to $+85°$ C. |
| Temperature Coefficient | .2 percent/°C. |

A second pyroelectric detector 35 is utilized to monitor source power. The specifications for detector 35 are as follows:

| Type | Pyroelectric |
| --- | --- |
| Wavelength Range | 0.9 to $12\mu$ |
| Element Size | 2 mm diameter |
| Permanent Window | $B_aF_2$ |
| NEP (0.9–$12\mu$, 34 Hz; 1 Hz BW) | $10^{-9}$ W/Hz$^{\frac{1}{2}}$ |
| Voltage Responsivity | 98 V/W |
| Temperature Range | $-20$ to $+85°$ C. |
| Temperature Coefficient | .2 percent/°C. |

Monitoring the average power in both beams can be accomplished at the end of the optical train using a beam splitter to extract a fraction of the total power and either a thermopile or thermistor bolometer to perform the average power measurement in each of the three wavelength intervals. An average power detector at this location would, however, have to perform a DC measurement and hence be extremely susceptible to ambient temperature drifts and changes in the ambient radiation levels entering through Windows W3 and W4. A more suitable location therefore, is in the transmitter enclosure monitoring the average powr in Beam B. A measurement of the average power in one beam suffices to determine exactly one-half the average power in both beams since the power in each beam is closely balanced. The accuracy required for the monitoring of the source power is not stringent hence some liberties may be taken with this measurement.

Only a fraction of the power in Beam B is required for the monitoring of source power. Pick-off mirror M6 is used to extract approximately one percent of the radiation in Beam B. A mirror (or possibly a lens) is used to image the radiation onto the sensing element of pyroelectric detector. The precautions previously indicated to prevent the generation of spurious signals and to eliminate noise sources within the primary detector housing also apply to the source monitor detector.

A separate three position filter wheel 34 must be utilized with the source monitor system if it is placed at this location. The wavelength isolation filters should be a close match to those used in the primary filter wheel. The two filter wheels 34, 36 are always moved in tandem, never separately controlled.

The performance of the chopper wheel 33 is critical to the operation of the extinctiometer. In all situations except heavy fog the residual unbalance in the two beams can be reduced to the minimum permitted by the performance of the chopper wheel. A maximum of 0.1 percent radiant power imbalance between the two beams is vital to achieving the performance objective of the instrument.

The pyroelectric detector senses any changes in radiant power incident on the chopper wheel. It therefore is not a sufficient condition for a "balance" that equal amounts of energy arrive at the detector during each half of a chop cycle. If the rate at which the equal amounts of energy arrive were to change in any way during the cycle a signal will be induced. Further, a difference in position of the two images on the sensing element causes an imbalance signal to occur since the radiation is alternating between the two beams. Accordingly, state of the art knife edges must be specified for the chopper blades. A high degree of flatness and uniformity of surface quality for each of the blades must also be achieved. Tolerances on the chopper wheel hub, the hub seat, drive shaft and bearings must be exacting.

The instrument design outlined herein makes an allowance for the possibility that a significantly better balance may be achieved with one blade over the other of a two-blade chopper. Signals from one or the other of the two blades may be processed independently to derive the extinction coefficient. If comparable balances are achieved with both blades then the data processing can proceed with both sets of data and achieve the same accuracy in half the time required if data from only one blade is used.

The ability to select the data acquired from one chopper blade or the other requires that the blades be coded in such a manner that an interrupter or reflecting sensor can distinguish between the two blades.

Position of the chopper wheel in the optical train is also a critical matter. Perfect knife-edge blades are not physically realizable. Hence, it is important that the cross-section of the beam to be chopped be as large as possible at the point of chopping. Chopping at a focal point is the least desirable situation. However, chopping at the largest possible beam diameter would require an inordinately large chopper wheel. The present design comprises between these two extremes by chopping at a point displaced several centimeters from a focal point in a divergent bundle of radiation.

The chopper wheel is located as close to the source as possible so that only source radiation is chopped. If the chopper were located near the detector chopped ambient radiation would be indistinguishable from the source radiation.

In accordance with the foregoing requirements the chopper wheel in the present example provides a 34 Hz chopping frequency using a two-blade reflective chopper with a 50 percent duty factor. An interrupt or reflective sensor (or sensors) must be employed to provide a reference signal (or signals) to the data processing system. Reference signals from the two blades shall be coded in a manner that will allow the data processing system to identify each blade. The specifications for this component are as follows:

| Motor Drive | |
|---|---|
| Frequency | 17 Hz |
| Stability (over 4 minute period) | .01 percent |
| Stability (long term) | .1 percent |
| Temperature Coefficient | 0.1 percent |
| Chopper Wheel Blades | |
| Type | Reflective |
| No. of Slots | 2 |
| Blade Openings | 90° ± 15 arc min. |
| Diameter | 4.5 inches |
| Surface Flatness | one-wave vane-to-vane |
| Mirror Coating | Gold |
| Mirror Reflectance ($1\mu$ to $12\mu$) | 98 percent |
| Blade Edges | Knife Edge |
| Knife Edge Angle | 40 degrees |
| Knife Edge Quality | State-of-Art |

Differences in transmission between the two paths of the device must be compensated if a suitable balance is to be achieved. A small polished steel rod on the end of a stepper-motor-driven micrometer screw 31 is used to achieve the balance. The diameter and length of penetration of the rod must be determined by experiment during fabrication of the instrument.

The optimum balance for one wavelength interval may not be the optimum for another wavelength interval. Hence, prior to the measurement period allotted to each wavelength interval the instrument should automatically adjust its balance for that particular wavelength interval.

Source 30 is a graybody source which must be housed in an enclosure to prevent rapid changes in source temperature due to air motion around the source. A window may be required on the enclosure if experience shows that an enclosure (with a necessary wide aperture) is not sufficient to reduce the rapid changes in temperature.

The source is imaged on a field-stop by relay optics. This feature is essential to restrict the area of the source which contributes to the radiation and to eliminate all contaminant radiation (e.g. from the source supports and the source enclosure).

The graybody source should be capable of sustained (very long life) operation at a temperature of 1400° K. or higher. The emissivity must be 0.9 or better over the wavelength range from 1 to 12 microns. The source must provide a circular area of at least 3 millimeters in diameter having a uniform temperature of 1400° K., or better, radiating into f/1.5 field-of-view.

The source size must be held to a minimum consistent with the above constraints. An oversize source will add unnecessarily to the electrical power demands of the instrument, create interference problems with adjacent optical components, and generate quantities of heated air which must be prevented from interfering with the internal function of the instrument and perturbing the sample volumes (either from heating of windows or modifying the ambient air by a venting system).

The air filtering system in the embodiment of FIG. 4 comprises an electrostatic fence that is constructed of coarse wire screening with needles attached at periodic intervals. A high voltage ( 12,000 volts, with non-lethal current capacity) is applied to the fence to create a corona discharge. The resultant electronic charge transfer processes result in a charge being deposited on any particles trying to penetrate the fence; and the partyicles are then repelled by the fence. Apparatus of this type is described in the literature reference of S. A. Hoenig, Applied Optics; Vol. 19, No. 5; 1 March 1980. Hoenig indicates that a cylindrical electrostatic fence surrounding a sample volume 50 centimeters long should exclude all dust, aerosol or fog particles, of the sizes of interest in the extinctiometer, in a matter of seconds.

Two cylindrical fences are used, one surrounding each of the sample volumes which are exposed to ambient air. Filtering of the air in one path or the other is accomplished by simply turing on one fence or the other. Both fences can be turned on for self-calibration of the instrument. A very-wide-mesh screen would surround the entire sampling area to prevent inquisitive persons from receiving the mild shock that would result from touching a live screen.

The filter wheel 36 is composed of three 120 degree segment filters forming a circular filter array. Metal webs at the junctions of the three filters are to be held to the minimum possible obscuration of the beam when the wheel is rotated from one filter position to the the next.

Each of the three filters is fabricated by deposition coatings on a substrate material appropriate to its particular band pass requirements. The thickness of all filters is identical (for mounting purposes) and determined by consultation with the supplier of the filters, due consideration being given to mechanical strength, mounting technique and range of operating temperature of the instrument. The specifications for filter channels 1, 2 and 3 are as follows:

| Channel 1 | |
|---|---|
| Filter Type | Square Bandpass |
| Substrate Material | Vendor Selected |
| Coatings | A/R Coated |
| Center Wavelength | $1.03\mu$ to $\pm$ 2 percent |
| Band Pass (Half Peak Trans.) | $0.98\mu$ to $1.08\mu$ $\pm$ percent |
| Peak Transmittance (Ave.) | 75 percent $\pm$ 5 percent |
| 0.1 Percent Transmittance (Absolute) | |
| Short (No less than) | $0.89\mu$ |
| Long (No greater than) | $1.20\mu$ |
| Blocking (Outside Range; 0.1 percent or better) | Complete; UV to $20.5\mu$ |
| Angle of Incident Radiation | Normal |
| Operating Temperature | $-25°$ C. to $+50°$ C. |
| Environmental Specifications: | |
| Humidity | per MIL-C-675A |
| Abrasion | per MIL-C-675A |
| Coating Adherence | per MIL-M-13508B |
| Channel 2 | |
| Filter Type | Square Bandpass |
| Substrate Material | Vendor Selected |
| Coatings | A/R Coated |
| Center Wavelength | $3.5\mu$ $\pm$ 2 percent |
| Band Pass (Half Peak Trans.) | $3.0\mu$ to $4.0\mu$ $\pm$ percent |
| Peak Transmittance (Ave.) | 75 percent $\pm$ 5 percent |
| 0.1 Percent Transmittance (Absolute) | |
| Short (No less than) | $2.7\mu$ |
| Long (No greater than) | $4.4\mu$ |
| Blocking (Outside Range; 0.1 percent or better) | Complete; UV to $20.5\mu$ |
| Angle of Incident Radiation | Normal |
| Operating Temperature | $-25°$ C. to $+50°$ C. |
| Environmental Specifications: | |
| Humidity | per MIL-C-675A |
| Abrasion | per MIL-C-675A |
| Coating Adherence | per MIL-M-13508B |
| Channel 3 | |
| Filter Type | Square Bandpass |
| Substrate Material | Vendor Selected |
| Coatings | A/R Coated |
| Center Wavelength | $10.0\mu$ $\pm$ 2 percent |
| Band Pass (Half Peak Trans.) | 8.0 to $12.0\mu$ $\pm$ 2 percent |
| Peak Transmittance (Ave.) | 75 percent $\pm$ 5 percent |
| 0.1 Percent Transmittance (Absolute) | |
| Short (No less than) | $7.3\mu$ |
| Long (No greater than) | $13.3\mu$ |
| Blocking (Outside Range; 0.1 percent or better) | Complete; UV to $20.5\mu$ |
| Angle of Incident Radiation | Normal |
| Operating Temperature | $-25°$ C. to $+50°$ C. |
| Environmental Specifications: | |
| Humidity | per MIL-C-675A |
| Abrasion | per MIL-C-675A |
| Coating Adherence | per MIL-M-13508B |

A design requirement of the optical system is that the transmittance of the system, including all mirrors, windows and the reflective chopper wheel, be 20 percent or better.

All mirrors should be gold coated. If a vapor deposition method for coating is used, a protective overcoat must be provided. If hard electroplated gold coatings are used then the protective overcoat requirement may be dropped. In either case the reflectance requirement is 98 percent or better for each mirror surface.

The four windows that define the sample volumes and which are exposed to the ambient environment must be made of Raytran ZnSe (or equivalent) having a nominal (polished) thickness of 4 millimeters. The detector enclosure window and (if required) the source enclosure window must be made of $BaF_2$ having a nominal thickness of 1 millimeter. All windows should be sufficiently oversize to avoid vignetting and stray light effects and provide for ease of alignment of the optical system.

While the invention has been described with reference to particular embodiments it is understood that the words which have been used are words of description rather than words of limitation and that changes within the purview of the appended claims may be made without departing from the scope and spirit of the invention in its broader aspects.

What is claimed is:

1. An atmospheric aerosol extinctiometer comprising
   a transmitter including light source means for generating a beam of radiant energy,
   a receiver including a first radiant energy detection means said detection means being positioned to receive said beam of radiant energy and having an output responsive to differences in received raidant energy beam power, said output being a function of the coefficient of extinction of ambient air under test,
   an optical system establishing first and second radiant energy beam paths between said light source means and said first radiant energy detecting means, said first and second beam paths alternately transversing a region of ambient air, beam switching means comprising a rotatable sector mirror in intercepting relationship with said beam for directing said beam alternately through said first and second beam paths, air filter means for filtering aerosols from the region of ambient air traversed by one of said beam paths, said air filter means being adapted to filter alternately the regions of ambient air traversed by said first and second beam paths, a second radiant energy detection means positioned to receive beam radiant energy, the output thereof comprising a monitor of beam power, synchronous pick up means monitoring sector mirror rotation, a processing electronic circuit receiving the outputs of said first and second radiant energy detector means and the output of said synchronous pick up means, said processing electronic circuit developing the coefficient of extinction $\gamma$ of ambient air under test by means of the equation $$\gamma = \frac{\sqrt{2}\,\pi R_o}{2R_f} \frac{V_{rmsB} - V_{rmsA}}{LV_{DC}}$$

$R_o$ being the DC responsivity of said first radiant energy detection means, $R_f$ being the responsivity at frequency f of said first radiant energy detection means, $V_{rms\ A}$ and $V_{rms\ B}$ corresponding to the ambient air under test in said first and second paths respectively, L being the length of the region of ambient air under test, and $V_{DC}$ is the DC signal output of said second radiant energy detection means, a first enclosed housing containing said transmitter, said first enclosed housing having a first window to accommodate said first beam path and a second window to accommodate said second beam path, and a second enclosed housing containing said receiver, said second enclosed housing having a third window to accommodate said first beam path and a fourth window to accommodate said second beam path, said first, second, third and fourth windows being ZnSe, said light source means comprising a graybody source operating at not less than 1400° K., and said first and second radiant energy detection means being pyroelectric detectors.

* * * * *